United States Patent [19]
Kulik et al.

[11] Patent Number: 4,765,311
[45] Date of Patent: Aug. 23, 1988

[54] WOUND RETRACTOR

[76] Inventors: Yaroslav P. Kulik, Ulitsa Zieskaya, 140, kv. 36, Blagoveschensk; Ivan I. Shmyrin, Prospekt Krasnogo Zanameni, 30, kv. 132, Vladivostok; Grigory M. Rutenburg, Ulitsa Lenina, 57, kv. 13, Blagoveschensk, all of U.S.S.R.

[21] Appl. No.: 38,205

[22] Filed: Apr. 14, 1987

[30] Foreign Application Priority Data

Apr. 24, 1986 [SU] U.S.S.R. ................. 4061958

[51] Int. Cl.⁴ .............................................. A61B 17/02
[52] U.S. Cl. ....................................... 128/3; 128/20
[58] Field of Search .......................... 128/343, 20, 3

[56] References Cited

FOREIGN PATENT DOCUMENTS 118747  8/1930  Austria ............................. 128/343

Primary Examiner—Michael H. Thaler
Attorney, Agent, or Firm—Burgess, Ryan & Wayne

[57] ABSTRACT

A wound retractor comprises a split tube made up of two halves, holders of the tube halves, a mechanism for spreading the tube halves apart, incorporating a retainer for locking the tube halves in position. The holder of one tube half is shaped as a plate having an oblong opening at the edge of which the tube half is located. The holder of the other tube half is shaped as a strip mounted slidably over the plate and having an opening similar to that in the plate. The second tube half is fitted at the edge of the strip opening opposite to the first tube half.

4 Claims, 1 Drawing Sheet

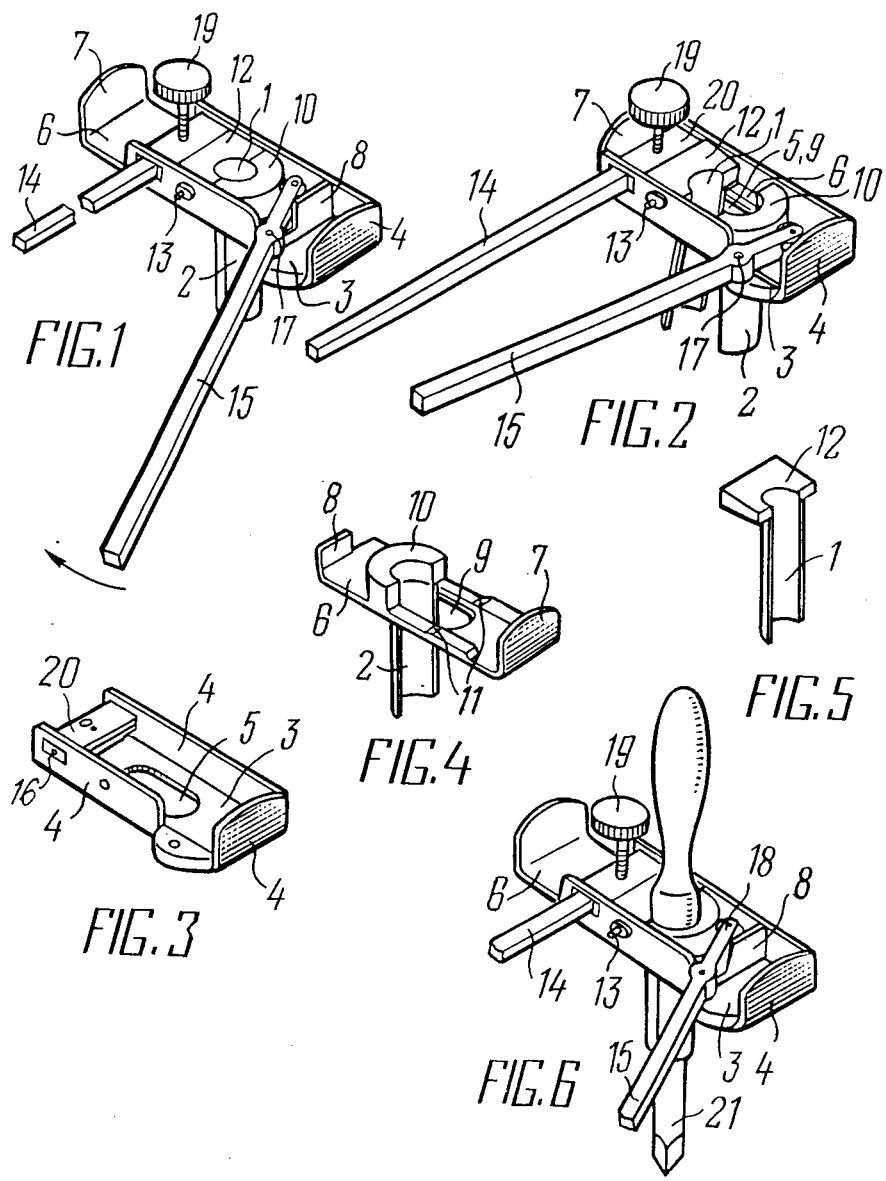

WOUND RETRACTOR

Field of the Invention

The invention relates generally to medical surgical instruments and more specifically to a wound retractor which is applicable for, e.g., laparoscopic manipulations, especially whenever it becomes necessary to bring a an organ to the surface of the abdominal wall (such as the stomach or gallbladder), or to remove it from the abdominal cavity (e.g., the vermiform appendix).

BACKGROUND ART

Wound retractors in the form of a fixed diameter (up to 11 mm) solid (nonsplit) tube are widely known to be used for cholecystostomy, gastrostomy, appendectomy, and in gynecological surgery. However, a fixed diameter of the heretofore-known wound retractors interferes with or renders some manipulations impracticable altogether. Thus, for instance, laparoscophic appendectomy involves the introduction of four wound retractors into patient's abdominal cavity, each of them being a fixed-diameter solid tube through which the stages of the appendectomy procedure are carried out with the aid of appropriate instruments (cf.'Endoscopy', v.15, No. 2, March 1983, New York, K. Semm, 'Endoscopy Appendectomy', pp. 59–64).

Another prior-art wound retractor is known to comprise a split tube made up of two halves, holders of the tube halves, and a mechanism for spreading the tube halves apart, provided with a retainer for the tube halves to lock in position (cf. Waldemar Link, Rectum- und Abdominal-Chirurgie, 1984, FIG. 20-1440).

In the known wound retractor the holders of the tube halves are shaped as curved rods held with their ends to the respective tube half so as to provide a possibility of turning the tube half about an axis passing through the point of rod-to-tube half holding. The mechanism for spreading the tube halves apart is in fact a micrometer screw interposed between the vacant ends of the holders of the tube halves.

The heretofore-known wound retractor suffers from an inadequately rigid construction which makes it impracticable for a majority of surgical procedures, such as, e.g., laparoscopic appendectomy.

Application of the heretofore-known wound retractor is fraught with cocking of the tube halves with respect to each other, which precludes introduction of surgical instruments through it and might result in expelling of the tube out of the wound. Besides, the holders might be bent with respect to the holding place of the mechanism for the tube halves spreading apart, which leads to departure from a preset distance between the set-apart tube halves, and affects adversely the reliability of holding the wound lips in place.

SUMMARY OF THE INVENTION

It is an object of the invention to provide a more reliable holding of the wound lips when applying a split-tube wound retractor.

It is another object of the invention to rule out a possibility of expelling the tube out of the wound.

It is one more object of the invention to provide a possibility of introducing the required surgical instruments through a split-tube wound retractor.

The essence of the invention resides in the fact that in a wound retractor, comprising a split tube, composed of two halves, holders of the tube halves, and a mechanism for spreading the tube halves apart, incorporating a retainer for locking the tube halves in position, according to the invention, the holder of the first tube half is shaped as a rectangular plate having flanges on its three sides, and an oblong opening arranged parallel to the longer sides of the plate, the first tube half being located at the flangeless side of the plate, the holder of the second tube half is shaped as a strip equal in size to the plate and having its own oblong opening similar to that in the plate, the second tube half being situated at the edge of the opening opposite to the first tube half, while the strip is mounted slidably over the surface of the plate lengthwise its longer sides so that when the strip is in one of its extreme positions, the first and second tube halves are brought in contact with each other to establish a solid tube having a minimum cross-section, while with the strip in the other extreme position, the tube halves are spread apart from each other a distance determined by the length of the oblong openings.

To provide higher reliability of holding the tube halves in the wound, it is expedient to provide wedgelike ridges on the strip along the longer sides of the opening so that the height of the ridges should increase towards that edge of the opening which is free from the tube half, it is also expedient that the tube half fitted in the plate opening be provided with a flange and be held together with the plate with a possibility of rocking motion about an axle arranged square with the flanges of the plate longer sides, and of interacting with the bevelled surfaces of the wedgelike ridges through the flange surface facing towards the strip.

To provide more convenience in operation with the wound retractor, the mechanism for spreading the tube halves apart is favourable to be made as two rods of which one is rigidly coupled to the plate, while the other is linked to the plate with a possibility of rocking about an axle secured in the plate and arranged square with its plane, and of interacting, through one of its ends, with the strip in order to impart reciprocating motion to the strip over the plate surface.

BRIEF DESCRIPTION OF THE DRAWINGS

In what follows the invention is illustrated in a detailed description of a specific embodiment thereof with reference to the accompanying drawings, wherein:

FIG. 1 is an isometric view of a wound retractor showing the tube halves when brought in contact with each other;

FIG. 2 is a view of FIG. 1 with the tube halves brought apart;

FIG. 3 is an isometric view of a plate;

FIG. 4 is an isometric view of a strip with a tube half;

FIG. 5 is an isometric view of a tube half with a flange; and

FIG. 6 is an isometric view of a wound retractor in assembly with a stilet, before the beginning of a surgical procedure.

DETAILED DESCRIPTION OF THE INVENTION

The wound retractor, according to the invention, as illustrated in FIGS. 1, 2, 3, 4, 5, comprises a tube made up of two halves 1 and 2 each set in its holder. The first holder is shaped as a rectangular plate 3 provided with flanges 4 on the three sides (two longer and a shorter one) and having an oblong oval-shaped opening 5 arranged parallel to the longer sides of the plate 3, the tube half 1 being located at the edge of said opening facing the flangeless side of the plate 3. The holder of the tube half 2 is shaped as a strip 6 equal in size to the plate 3, having a flange 7 on one of the shorter sides thereof and a stop 8 on the opposite side, as well as an oblong oval-shaped opening 9 similar to the opening 5 in the plate 3, the tube half 2 being situated at the edge of said opening opposite to the side of the strip 6 provided with the stop 8, said tube half having a projection 10 above the surface of the strip 6. Further, wedgelike ridges 11 are provided lengthwise of the longer sides of the opening 9, the height of said ridges increasing towards the edge of the opening 9 free from the tube half. The tube half 1 is provided with a flange 12 and is fitted in the opening 5 of the plate 3 with a possibility of rocking about an axle 13 arranged square with the flanges 4 of the longer sides of the plate 3. The mechanism for spreading the tube halves 1, 2 apart is composed of two rods 14 and 15 of which the rod 14 is rigidly coupled to the plate 3 through a threaded joint having a socket 16, while the rod 15 is linked to the plate 3 with a possibility of rocking about an axle 17 secured in the plate 3 and arranged square with the plane thereof, and of interacting, through an end 18, with the stop 8 of the strip 6, or with the projection 10 of the tube half 2 in order to impart reciprocating motion to the strip 6 over the surface of the plate 3 lengthwise the flanges of the longer sides thereof.

The strip 6 is mounted slidably over the surface of the plate 3 so that when it is in one of its extreme positions, the tube halves 1, 2 are brought in contact with each other, thus establishing a solid tube having a minimum cross-section, while with the strip in the other extreme position, the tube halves are spread apart from each other a distance determined by the length of the oblong openings 5 and 9. With the strip 6 in such a position, the openings 5 and 9 are brought in alignment and are arranged one above the other.

The wound retractor, according to the invention, is also provided with a retainer adapted to lock the tube halves 1, 2 in position and made as a locking screw 19 and a cross-web 20 having a tapped hole to receive the screw 19 and forced into the flanges 4 of the plate 3 so that a gap is left in between the cross-web 20 and the surface of the plate 3, somewhat in excess of the thickness of the strip 6, said gap being for the strip 6 to freely slide over the surface of the plate 3.

The wound retractor according to the invention operates as follows.

The rod 15 is moved to bring the tube halves 1, 2 in contact with each other. The strip 6 is locked in that position with the locking screw 19 by turning it into the tapped hole in the cross-web 20 until it thrusts against the surface of the strip 6. Then a stilet 21 is introduced into the tube (the wound retractor in such a position being represented in FIG. 6), and a puncture is made, e.g., of the patient's anterior abdominal wall, whereupon the stilet 21 is withdrawn. Next the locking screw 19 is loosened, and the slidable strip 6 is displaced, using the rod 15, by acting with its end 18 upon the stop 8. As a result, the tube half 2 is disengaged from the tube half 1. With the strip 6 sliding, the wedgelike ridges 11 interact, by virtue of their bevelled surfaces, with the surface of the flange 12 that faces towards said ridges, whereby the rocking tube half 1 assumes an angular position, the angle being open into the abdominal cavity with respect to the tube half 2. Upon bringing the tube halves 1, 2 apart from each other for a required distance, the slidable strip 6 is locked in that position with the locking screw 19 (the wound retractor in such a position being shown in FIG. 2). The wound retractor, according to the invention, holds the wound lips firmly, thus providing a wide approach to the organ being operated upon, enables one to introduce various surgical instruments into the wound and is reliably retained in the wound due to an angular position of the tube half 1.

What is claimed is:

1. A wound retractor, comprising:
    a split tube including a first half of said tube and a second half of said tube;
    a holder of said first tube half; said holder shaped as a rectangular plate having two longer and two shorter sides;
    said plate including flanges on said two longer sides and on one of said shorter sides thereof;
    said plate including an oblong opening arranged lengthwise said longer sides of said plate and having two edges opposite to each other lengthwise the opening;
    said first tube half fitted in said opening at an edge thereof proximal to said shorter plate side devoid of a flange;
    a holder of said second tube half;
    said holder of said second tube half-shaped as a rectangular strip equal in size to said plate and mounted slidably over the surface of said plate lengthwise said longer sides thereof;
    said strip including another oblong opening similar to said opening in said plate and having two edges opposite to each other lengthwise the opening;
    said second tube half fitted in said opening in the strip at an edge thereof opposite to said first tube half;
    said strip, while performing a sliding motion over the surface of said plate, being capable of assuming one of two extreme positions with respect to said plate, wherein said tube halves are brought in contact with each other to form a solid tube having a minimum cross-section in one extreme position, and in the other extreme position, said oblong openings are brought in alignment and are arranged one above the other, while said tube halves are situated opposite to each other and set apart a distance determined by the length of the oblong openings;
    means for spreading said tube halves apart; and
    retainer means for locking said tube halves in position.

2. A wound retractor as claimed in claim 1, further comprising:
    wedgelike ridges located on said strip lengthwise the longer sides of said another oblong opening, said ridges having a height increasing towards said edge of said opening free from said second tube half, each of said ridges having a bevelled surface;
    a flange with which said first tube half is provided, said flange having a surface situated above said plate and facing towards the latter;
    said first tube half fitted in said opening of the plate with a possibility of rocking with respect to said plate about an axle arranged square with said flanges of said longer sides of said plate, and also of interacting, during said sliding motion of the strip, with said bevelled surfaces of said wedgelike ridges through said surface of said flange that faces towards said strip.

3. A wound retractor as claimed in claim 1, wherein said mechanism for spreading said tube halves apart comprises:
- a first rod rigidly coupled to said plate;
- a second rod which is essentially a double-arm rocker having a rocking axle held to said plate and square with its plane, one of the arms of said rocker being capable of interacting with said strip to impart said sliding motion thereto over the surface of said plate.

4. A wound retractor as claimed in claim 2, wherein said mechanism for spreading said tube halves apart comprises:
- a first rod rigidly coupled to said plate;
- a second rod which is essentially a double-arm rocker having a rocking axle held to said plate and square with its plane, one of the arms of said rocker being capable of interacting with said strip to impart said sliding motion thereto over the surface of said plate.

* * * * *